United States Patent [19]

Goh et al.

[11] Patent Number: 5,419,328

[45] Date of Patent: May 30, 1995

[54] MEAN SQUARED SPEED AND MYOCARDIAL PERFORMANCE

[75] Inventors: Christiana Goh, Montclair; Hewlett E. Melton, Jr., Sunnyvale, both of Calif.

[73] Assignee: Hewlett-Packard Company, Palo Alto, Calif.

[21] Appl. No.: 104,292

[22] Filed: Aug. 9, 1993

[51] Int. Cl.⁶ ............................................. A61B 8/00
[52] U.S. Cl. .............................................. 128/660.07
[58] Field of Search ................. 128/660.01, 660.04, 128/660.07, 661.09–661.10

[56] References Cited

U.S. PATENT DOCUMENTS

| | | | |
|---|---|---|---|
| 4,896,674 | 1/1990 | Seo | 128/661.09 |
| 5,014,710 | 5/1991 | Maslak et al. | 128/661.09 X |
| 5,148,809 | 9/1992 | Biegeleisen-Knight et al. | 128/660.07 |
| 5,170,170 | 12/1992 | Soumekh | 342/179 |
| 5,190,044 | 3/1993 | Kawasaki et al. | 128/661.09 |
| 5,224,481 | 7/1993 | Ishihara et al. | 128/660.07 |
| 5,233,993 | 8/1993 | Kawano | 128/660.07 |
| 5,257,626 | 11/1993 | Pelc et al. | 128/661.09 X |
| 5,285,788 | 2/1994 | Arenson et al. | 128/660.07 X |

OTHER PUBLICATIONS

Kuecherer, Helmut F., et al., "Two-dimensional Echocardiographic Phase Analysis," *Circulation*, vol. 85, No. 1, Jan. 1992, pp. 130–142.

Wickline, Samuel A., et al., "The dependence of myocardial ultra-sonic integrated backscatter on contractile performance," *Circulation*, vol. 72, No. 1, Jul. 1985, pp. 183–192.

*Primary Examiner*—Francis Jaworski

[57] ABSTRACT

A method and system of monitoring performance of a heart include echocardiographic transmission and reception to form time series of frames containing mean squared difference data. Mean squared signal change, mean squared speed or root mean squared speed may be used to form functional images, such as average speed over a selected time interval or peak speed over a selected time interval.

18 Claims, 5 Drawing Sheets

MEAN SQUARED SPEED AND MYOCARDIAL PERFORMANCE

Technical Field

The present invention relates generally to monitoring heart performance and more particularly to methods and systems for echocardiographic imaging.

BACKGROUND ART

Traditional approaches for assessing myocardial performance, either on a global or regional level, impose limitations on both the degree and the ease of analysis that can take place. Assessing regional function is typically accomplished by analyzing wall motion using echocardiography, Magnetic Resonance Imaging (MRI), fast CT, or bi-plane cine radiographs. Most of these approaches do not allow assessment of the vigor of regional contraction performance during systole, the regional rates of change associated with either contraction or relaxation, performance averaged over a cardiac cycle, or changes in regional myocardial performance from one beat to the next beat.

In echocardiography, more rigorous assessment typically requires manual measurements of variables such as wall thickness. Other methods of quantitative assessment currently being investigated include the use of doppler, which has traditionally been used for measuring blood flow velocities, for measuring myocardial velocities. Unfortunately, doppler technology is inherently limited because it is accurate only when motion is directed along a line of sight of a transducer. There is also a dependence upon the angle between the line of sight and the motion, such that large errors in measurement occur when motion is directed perpendicular to the line of sight. Moreover, current doppler processing of a 90 degree sector limits the frame rate to approximately 12 Hz, such that appreciation of many cardiac events is limited.

It is an object of the present invention to provide a method and system for the assessment of regional performance of a heart, wherein the limitations of current technology and methods are overcome.

SUMMARY OF THE INVENTION

The above object has been met by an echocardiographic method and system that utilize regional speed measurements in real-time echocardiograms to assess regional myocardial performance. The approach is to form a first time series of frames, to determine mean squared difference data among the frames in monitoring cardiac motion, and then to measure mean squared speed or root mean squared speed. These resulting measurements are directly related to that which is of interest—cardiac motion.

The frames of the first time series are sets of data points that are a function of the envelope of the return signal (S) from specific sites of a patient's heart. A second time series of frames is generated from the first by determining on a data point-by-data point basis the difference between data point values of temporally adjacent frames in the first time series. The point value differences are squared to obtain square rate of signal change data $$\left(\frac{dS}{dt}\right)^2$$

for each data point in the frames of the second time series.

A third time series of frames may be generated from the second time series by averaging $$\left(\frac{dS}{dt}\right)^2$$

for each data point in the second time series with the $$\left(\frac{dS}{dt}\right)^2$$

values of data points in the neighborhood in which the data point of interest resides. As a result, the third time series will contain mean squared rate of signal change data.

The third time series of frames may be used as functional images of cardiac motion. Alternatively, a "temporal average" image can be produced by averaging corresponding data point values for some or all of the frames on a point-by-point basis. The resulting temporal average is a single functional image of time-averaged mean squared rate of signal change. A "peak" image can be formed by generating a single functional image from peak values on a data point-by-data point basis for the third time series of frames. Harmonic processing may also be employed to generate analytical data or to provide functional images.

As yet another alternative, a time series of frames of speed data can be generated where speed is defined as the magnitude of the vector velocity v. This time series may contain either root mean squared speed data (m) or mean squared speed data ($v^2$). In the preferred embodiment, when the echocardiographic signals (S) have space and time dependence, S (x, y, z, t), the mean squared rate of signal change in the third time series is analytically defined as:

$$\overline{\left(\frac{\partial S}{\partial t}\right)^2} = \overline{\left(\frac{\partial S}{\partial x}\right)^2} v_x^2 + \overline{\left(\frac{\partial S}{\partial y}\right)^2} v_y^2 + \overline{\left(\frac{\partial S}{\partial z}\right)^2} v_z^2.$$

This equation shows a relationship between the mean squared rate of signal change and the mean squared speed of motion for each direction $v_{(x,y,z)}^2$, with mean squared gradient components, $$\overline{\left(\frac{\partial S}{\partial (x,y,z)}\right)^2},$$

as constants of proportionality. If the beam width is equal to the pulse length, a spherical interrogation volume is obtained and the respective gradient components are all the same in a mean squared sense, i.e.:

$$\overline{\left(\frac{\partial S}{\partial x}\right)^2} = \overline{\left(\frac{\partial S}{\partial y}\right)^2} = \overline{\left(\frac{\partial S}{\partial z}\right)^2}.$$

A mean squared gradient processor may be used to obtain a series of frames of mean squared gradient data $$\overline{\left(\frac{dS}{dg}\right)^2}$$

from the first time series. The processing includes determining the difference between data point values of a selected data point and an adjacent data point. This determination can be performed in a single coordinate direction (i.e., dg is equal to dx or dy) from the selected data point or can be an average of differences in more than one coordinate direction (i.e., dg is an average of dx and dy) from the selected data point. The determination is repeated for each selected data point in order to obtain a $$\frac{dS}{dg}$$

value for individual data points of the frames of the first time series. The time series of frames of speed data can then be generated on a point-by-point basis by dividing the mean squared rate of signal change by the mean squared gradient and then taking the square root, i.e.:

$$m = (|v|^2)^{0.5} = \left\{ \overline{\frac{dS^2}{dt}} \bigg/ \overline{\frac{dS^2}{dg}} \right\}^{0.5}.$$

The time series of frames of speed data is a series of functional images of root mean squared speed or mean squared speed data. In the same manner that a temporal average image or a peak image or a harmonic image was described as being formed from the third time series, such images can be formed from the time series of speed data.

An advantage of the present invention is that the approach does not require frame-by-frame, computer assisted manual measurements. Instead real-time regional measurements can be utilized to determine the vigor of regional motion of myocardium such as regional contraction rates. In addition, regional relaxation rates, regional peak speed, regional speed averaged over some selected time interval, and regional speed changes from beat-to-beat can also be appreciated in functional images. Regional measurements can be appreciated by displaying waveforms of either mean squared rate of signal change or root mean squared speed in real-time. For each frame in either the third time series or the time series of speed data, the average values within a user-defined region of interest can be displayed. Analysis of cardiac performance may be a comparison of the average values of different regions of interest.

BEST MODE FOR CARRYING OUT THE INVENTION

Figure 1:
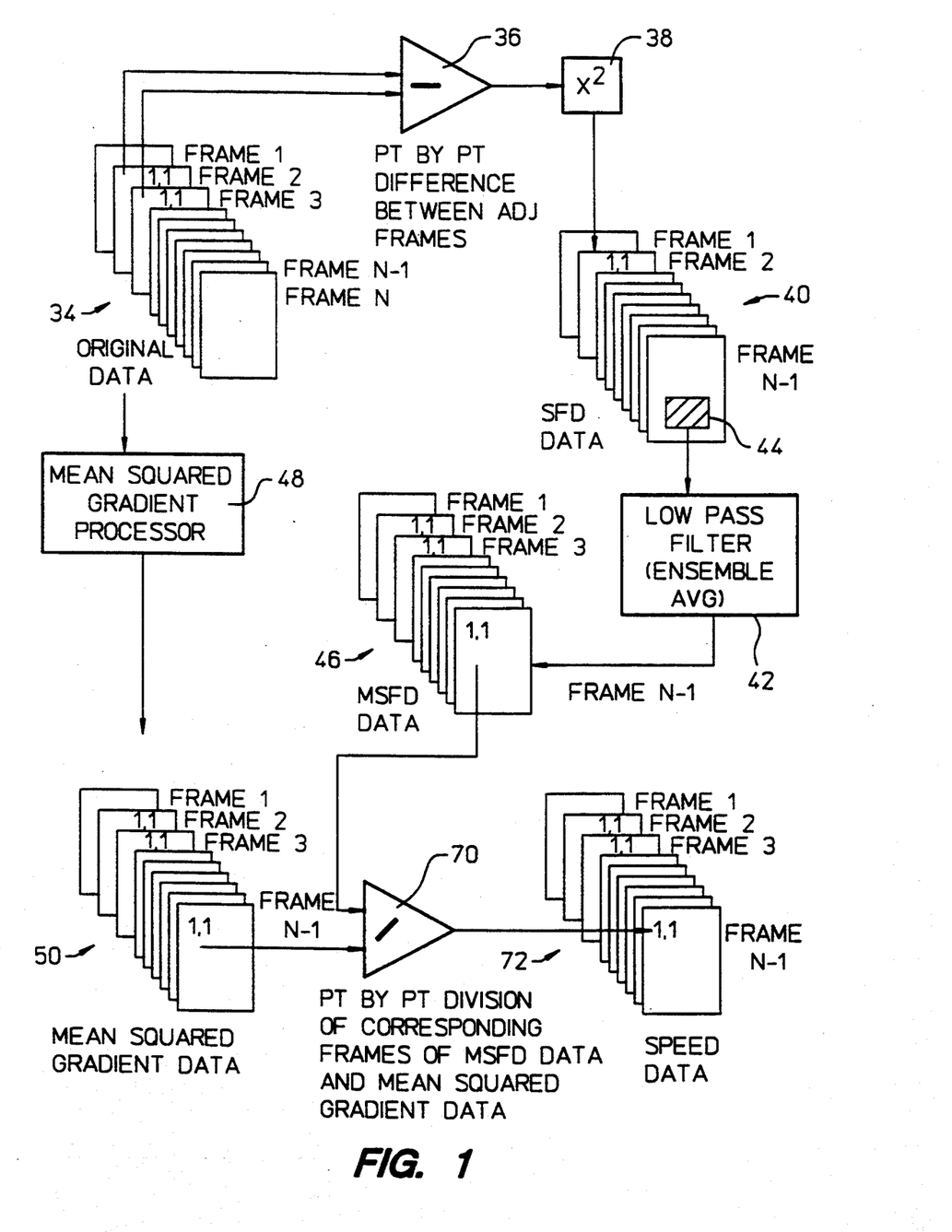
FIG. 1 is a schematical view of a sequence of signal processing to obtain speed data in accordance with the present invention.

With reference to FIG. 1, standard echocardiographic equipment is utilized to transmit ultrasonic signals into a patient and receive ultrasonic reflections to form a first time series of frames 34 of data. The echocardiographic equipment is directed to obtain data responsive to operation of the heart of the patient.

Merely for example, raw data from the echocardiographic equipment can be acquired in the form of 121 acoustic lines of data having a spacing of 0.75°, with the first line starting at an angle of −45° from straight ahead. The envelope and the magnitude of the raw data are computed and used as the data of the first time series 34. This data may then be scanconverted to x, y coordinate data for processing and viewing. The raw data may be acquired using echocaediographic equipment having an array of ultrasonic transducers or a single mechanically scanned transducer.

As will be discussed more fully below, the processing steps of FIG. 1 are carried out to obtain frames of speed data. In a preferred embodiment, the speed data are either mean squared speed or root mean squared speed. Regional speed measurements in real-time echocardiograms that are sensitive to all directions of myocardial motion may be utilized to monitor performance of the heart, since mean squared speed and root mean squared speed are directly related to motion of the heart.

Measuring speed for the purpose of assessing myocardial performance is accomplished with the use of the continuity equation applied to the ultrasonic backscatter from myocardium. Beginning with the backscatter signal having space and time dependence, $S(x,y,z,t)$, the associated continuity equation is as follows:

$$\frac{dS}{dt} = (\nabla S) \cdot \vec{v} + \frac{\partial S}{\partial t} \qquad \text{EQ. (1)}$$

where v is the vector velocity. In ultrasonic echocardiography, $$\frac{dS}{dt}$$

will be equal to 0 when there is no sink or source of power during propagation of the return signal. This leaves the following relationship:

$$\frac{\partial S}{\partial t} = -\nabla S \cdot \vec{v} \qquad \text{EQ. (2)}$$

This last equation shows the relationships among the rate of change of signal, $$\frac{\partial S}{\partial t},$$

the spatial gradient, $\nabla S$, and the vector velocity, $\vec{v}$. By forming an ensemble average of the square of the last equation, the mean square rate of change is found:

$$\overline{\left(\frac{\partial S}{\partial t}\right)^2} = \overline{\left(\frac{\partial S}{\partial x}\right)^2} v_x^2 + \overline{\left(\frac{\partial S}{\partial y}\right)^2} v_y^2 + \overline{\left(\frac{\partial S}{\partial z}\right)^2} v_z^2 \quad \text{EQ. (3)}$$

EQ. (3) shows a relationship between the mean squared rate of change of the signal and the mean squared speed of motion for each direction, $V_{(x,y,z)}^2$, with the mean squared gradient components, $$\overline{\left(\frac{\partial S}{\partial(x,y,z)}\right)^2},$$

as constants of proportionality. The bars in the equation denote an ensemble average. It can be seen that the mean squared rate of signal change provides a relative measure for speed of motion whereby regional deficiencies in myocardial motion can be appreciated in relation to normally moving myocardium. Thus, an improved method of assessing regional performance of myocardium has been developed.

In FIG. 1, the first time series 34 of frames of echocardiographic data is formed throughout one or more cardiac cycles. A first processing 36 occurs on a data point-by-data point basis to determine signal change between adjacent frames. In FIG. 1, data point 1,1 of Frame 2 is compared with data point 1,1 of Frame 3 to determine the signal change between the frames at that data point. A second processing 38 squares the difference of signals obtained at the first processing 36. The value of the squared difference is then assigned to data point 1,1 of Frame 2 in a new time series 40. The time series 40 has one fewer frame than the time series 34, since each frame in the second time series is formed by the comparison of two frames in the first time series.

The second time series 40 is a sequence of square of frame differences ("SFD"). Each SFD frame may be spatially low-pass filtered to obtain an ensemble average at 42 for a region 44 of the SFD frame. Thus, each data point is averaged with adjacent data points in the region 44.

The ensemble averaging at 42 is employed to form a third time series 46 on a point-by-point basis. Each frame in the third time series 46 corresponds temporally with a frame in the second time series 40. However, the third time series contains estimates of the mean squared rate of signal change ("MSFD"). Therefore, the frames are a series of functional images of myocardial operation throughout one or more cardiac cycles.

The gradient components are related to the beam widths and the pulse length. The beam widths and pulse length can be designed to provide respective gradient components which are all the same in a mean squared sense, i.e. the beam widths in azimuth and in elevation are the same and are equal to the pulse length, so that:

$$\overline{\left(\frac{\partial S}{\partial x}\right)^2} = \overline{\left(\frac{\partial S}{\partial y}\right)^2} = \overline{\left(\frac{\partial S}{\partial z}\right)^2}. \quad \text{EQ. (4)}$$

Figure 2:
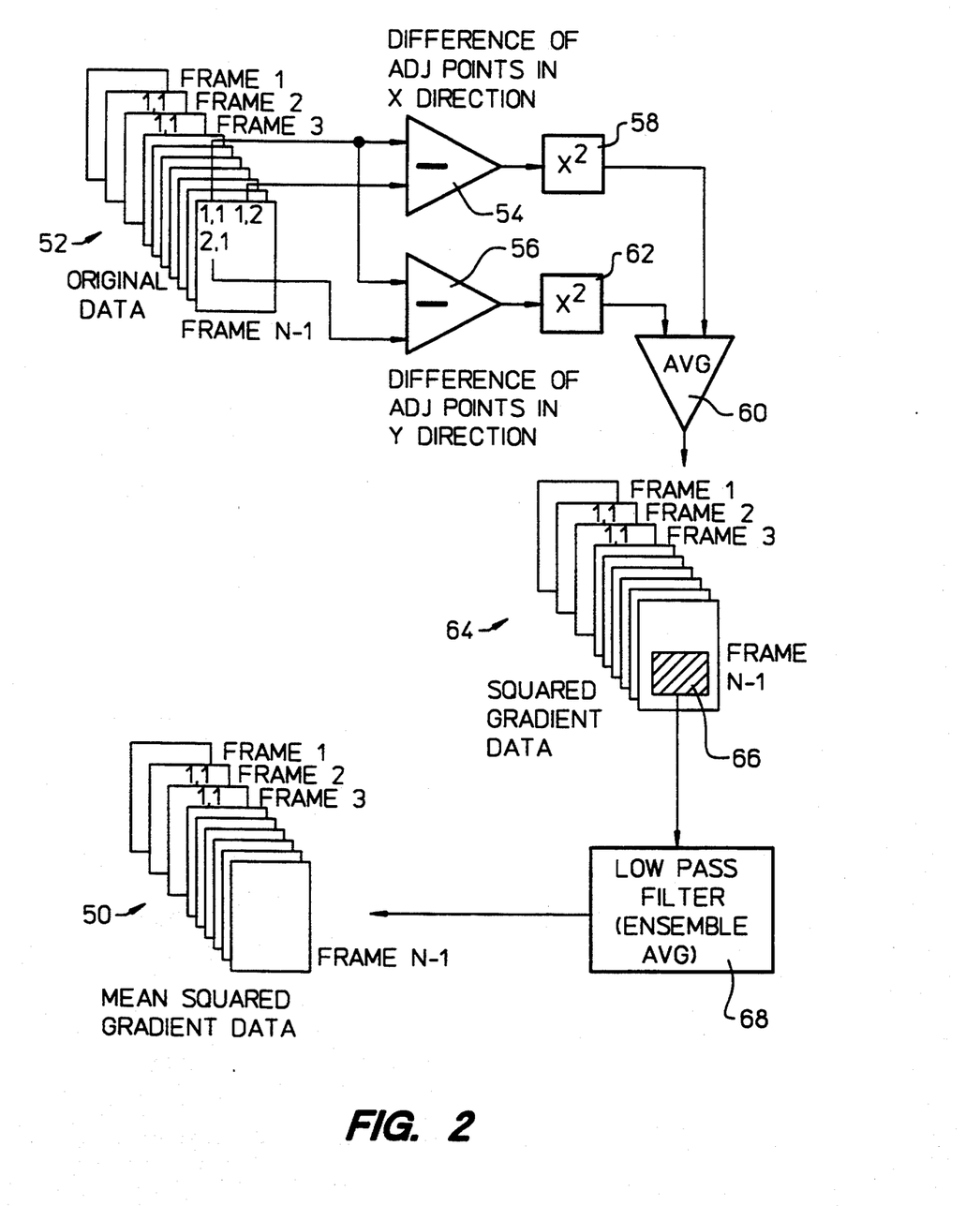
FIG. 2 is a schematical view of one embodiment of a mean squared gradient processor of FIG. 1.

FIG. 1 shows a mean squared gradient processor 48 that is utilized to obtain a fourth time series of frames 50. The fourth time series comprises frames of data related to one or more of the mean squared gradients of EQ. (3). FIG. 2 shows an embodiment of the processor that utilizes changes in both the x direction and the y direction to obtain the mean squared gradient data of the fourth time series of frames 50. The processor begins with frames 52 of original data. The frames 52 may be the same ones as the first time series 34 of FIG. 1, with the final Frame N being disregarded. Alternatively, after a computation of the gradient data, temporally adjacent frames in the first time series 50 may be averaged on a data point-by-data point basis to reduce the number of frames to N−1.

The mean squared gradient processor 48 includes circuitry 54 for determining the difference between data points of a frame in the x direction. Simultaneously, circuitry 56 determines the difference between adjacent data points in the y direction. The difference value determined at 54 is squared at circuit 58 to provide a first input to a gradient averager 60. A second input to the averager is obtained by squaring the difference value from 56 at a squaring circuit 62.

The output of the gradient averager 60 is employed to form frames 64 of squared gradient data. For each frame 52 of original data, the gradient averaging is carried out in a data point-by-data point manner to generate the N−1 frames 64.

Ensemble averaging takes place at a low pass filter 68 for a region 66 of a selected size. Therefore, each data point in the fourth time series of frames 50 is an ensemble average of a corresponding data point and its 10 surrounding data points from a frame 64.

As previously noted in referring to EQ. (4), in the ideal, the interrogation volume can be designed so that all of the gradient components are equal in a mean squared sense. Therefore, in the ideal the outputs from 58, 60 and 62 are equal. However, the gradient averager 60 may be utilized to reduce the adverse effects of noise generated in non-ideal circumstances.

For FIGS. 1 and 2, the mean squared gradient data of frames 50 will be referred to herein as $$\overline{\left(\frac{dS}{dg}\right)^2}$$

data, which may be determined by a signal change in a single coordinate direction or in more than one direction, as in the embodiment of FIG. 2. In this case, using EQ. (3) and EQ. (4) the mean squared speed or root mean squared speed (m) can then be estimated on a data point-by-data point basis by dividing the time-averaged mean squared rate of signal change data of frames 46 by the mean squared gradient data of frames 50 and then taking the square root, i.e.

$$m = \{|v|^2\}^{0.5} = \left\{ \left(\overline{\left(\frac{dS}{dt}\right)^2}\right) \Big/ \left(\overline{\left(\frac{dS}{dg}\right)^2}\right) \right\}^{0.5}. \quad \text{EQ. (5)}$$

The point-by-point division occurs at circuit 70 to generate a fifth time series of frames 72 of speed data.

The fifth time series of frames comprises functional images of mean squared speed or root mean squared speed. Thus, direct quantification of performance is provided.

Figure 3:
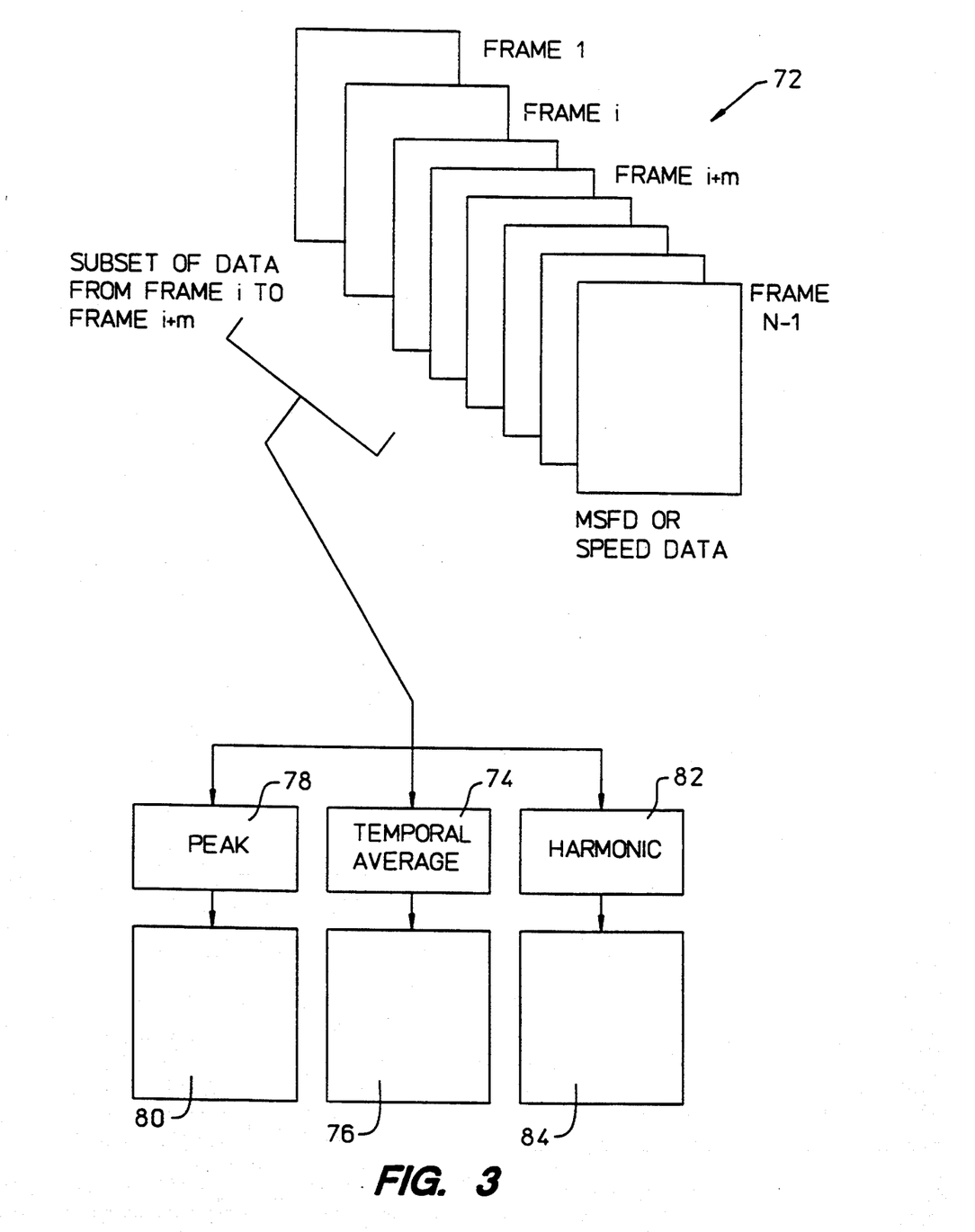
FIG. 3 is a schematical view showing the generation of functional images in accordance with the present invention.

Referring now to FIG. 3, temporal averaging 74 across at least some of the frames of either the third or fifth time series 46 or 72 on a data point-by-data point basis produces a single functional image 76 of time averaged regional myocardial speed. Generating the functional image can be limited to an interval within a cardiac cycle, such as a systolic interval from Frame i to Frame i+m, so that regional contraction performance of the myocardium can be appreciated. Alternatively, the subset of frames can be a limitation of the frames that image the relaxation portion of the cardiac cycle, so that diastolic performance can be appreciated. Regional average speed can be used to form a functional image for a complete cardiac cycle for use in examining speed differences from one heartbeat to the next. Optionally, peak regional speed can be determined at 78 in order to form a single functional image 80. The determination of peak speed can be limited to some interval, such as the systolic interval or the diastolic interval, in the same manner as the use of the average speed at 74.

Any of the functional images 74, 78 and 82 in FIG. 3 may be obtained for two or more cardiac cycles for the assessment of performance on beat-to-beat basis. This holds special interest in cases of arrhythmia, ischemia, infarction or with electrophysiologic defects.

Time-averaged, mean squared rate of signal change from frames 46 and speed data from frames 72 can be used for assessment of regional myocardial performance in the form of functional images for systole, diastole, a complete cycle, or beat-to-beat variations. Peak values during systole and during diastole can be used to form functional images, or separate images can be formed to determine beat-to-beat variations. In addition, when the mean squared gradients are all equal, quantitative functional images can be made for speed for any of these aspects of performance.

Another approach identified in FIG. 3 is referred to as harmonic processing 82 to obtain a functional image 84. The data of either the third or fifth time series 46 or 72 may be analyzed for each point across the N−1 frames of data or some subset thereof, thereby obtaining a time sequence of data. For example, the subset may be the systolic interval from the Frame (i) prior to the closing of the mitral valve at the onset of systolic contraction to the Frame (i+m) prior to the opening of the mitral valve at the onset of diastolic filling. The time sequence of data taken from the same point in each frame is treated as a time series and the spectral components are extracted using a Fourier transform. Extracting only the dc term from the spectral data for each spatial point gives a single frame of data averaged over time. This single frame of data may be used to render a sensible portrait of myocardial motion in the same manner as described above. However, additional detail of myocardial performance at the fundamental level of the contraction-relaxation cycle can be obtained by extracting the first harmonic from the spectral data covering a cardiac cycle so as to form another sensible portrait for the cyclic motion of the myocardium.

Figure 4:
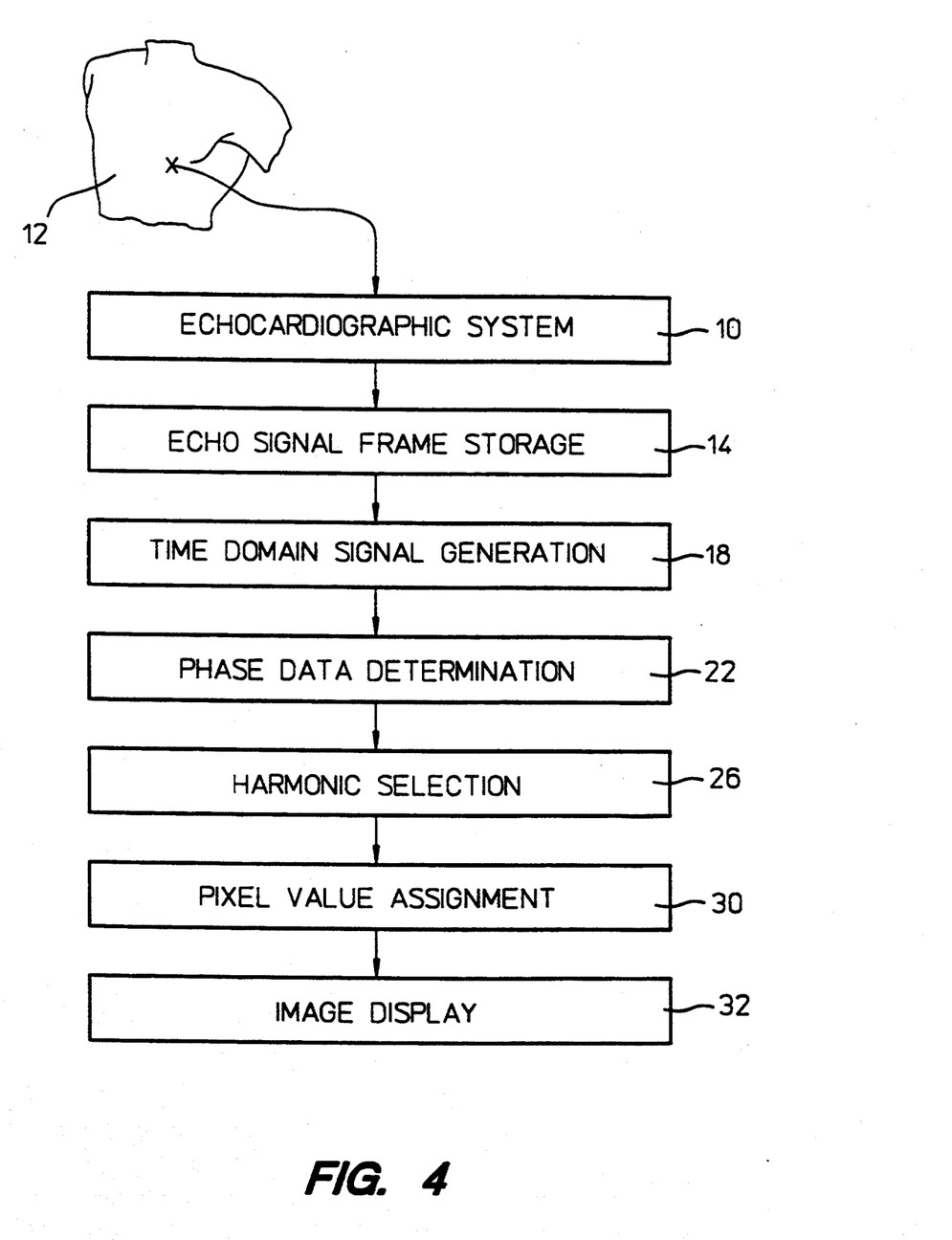
FIG. 4 is a flow chart of a method and system for monitoring and imaging performance of a heart.
Figure 5:
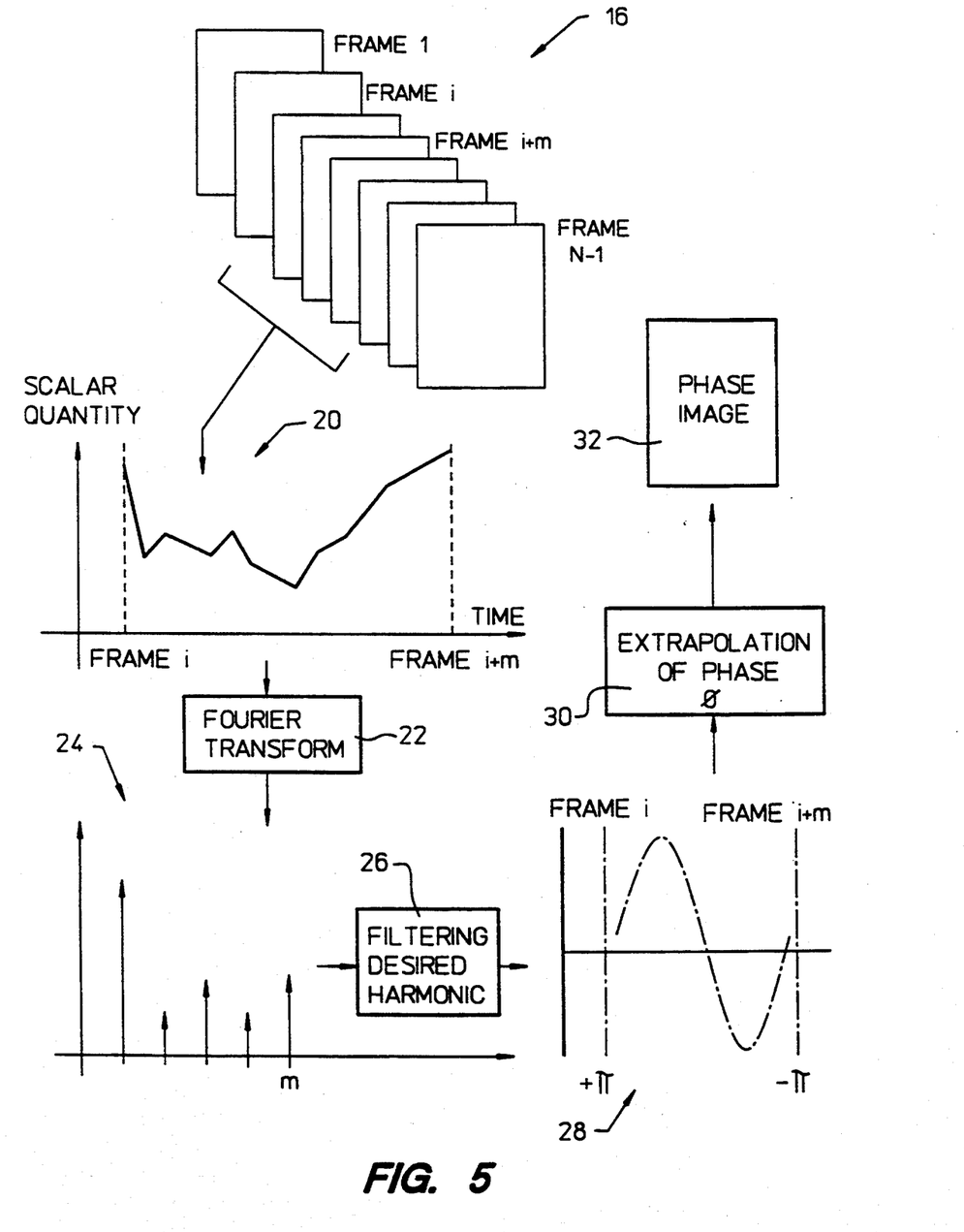
FIG. 5 is a schematical view a sequence of signal processing for carrying out the system of FIG. 4.

Yet another approach is shown in FIGS. 4 and 5. This approach is referred to as phase imaging. An echocardiographic system 10 transmits ultrasonic signals to a patient 12 and receives ultrasonic reflections. The frame storage 14 will include the processing for obtaining the time series 16 of FIG. 5. The time series 16 may be either one of the time series 46 or the time series 72 of FIG. 3. Then, for each set of data points which corresponds to a specific site of the patient's heart, the data point values are plotted from frame to frame. In FIG. 4, this is shown as time domain signal generation 18, while in FIG. 5 a single time domain signal 20 is shown. Ideally, each data point in a frame within the time series 16 is used in plotting a time-varying signal such as that shown at 20, thereby yielding a number of time domain signals corresponding to the number of data points in a frame. However, the plotting of time-domain signals may be limited to data points corresponding to specified regions of the heart, if desired.

As shown in FIGS. 4 and 5, a Fourier transformation 22 is then performed on each time domain signal 20 to obtain a transform 24 from the particular time domain signal. For the transform 24, each harmonic has an associated magnitude and phase. A filter 26 is then employed to obtain a single phase value and a single magnitude value of the desired harmonic. Typically, the first harmonic is selected since for a given periodic function, the magnitude of the first harmonic is typically largest. However, the present invention is not limited to the selection of the first harmonic. If there is a stronger higher harmonic, such as a second harmonic, it could also be used to ascertain a phase angle. For mean squared speed, the second harmonic is potentially very important. Since mean squared speed is a function of velocity squared, the strongest harmonic of the velocity squared curve at 20 is theoretically the second harmonic, assuming that the strongest harmonic of the velocity (unsquared) curve plotted over the cardiac cycle is the first harmonic.

In selecting a harmonic other than the first, the problem of phase wrapping must be considered[. For example, where assigned phase values are to be within the range of $-\pi$ to $+\pi$ and the second harmonic is the harmonic of interest, activations that occur at two different times corresponding to $\pi/4$ and $9\pi/4$ will appear to have the same phase of $\pi/4$. Phase unwrapping techniques may be required to decipher a phase portrait generated with a second or higher harmonic.

In the study of cardiac motion, information regarding a particular event of a cardiac cycle is primarily contained during the interval in which the event occurs. However, over the entire cardiac cycle other major cardiac events may influence the magnitude and the phase of the selected harmonic. For example, for two different hearts having the same systolic contraction sequence, the characteristics of diastolic filling and atrial kick may differ, thereby affecting the phase of the first harmonic. One way to preclude such extraneous influences in measuring the cardiac contraction sequence is to limit the monitoring of the selected scalar to the systolic interval from the Frame (i) prior to the closing of the mitral valve at the onset of systolic contraction to the Frame (i+m) prior to the opening of the mitral valve at the onset of diastolic filling.

Data is fit to a wave 28 to delineate the sequence of activity. Thus, a phase angle extrapolation and pixel value assignment 30 is performed on a pixel-by-pixel basis to form a phase image 32. That is, for each time domain signal 20, a pixel value is assigned according to a phase angle extracted by the processing of the time domain signal. Processing by means of Fourier transforms is not critical to the present invention. Other methods of extrapolating a phase angle from the time domain signal 20 are known and may be employed. That is, in FIG. 5, the extrapolation 30 may be performed directly from the signal 20.

Each pixel of the phase image 32 is encoded with its corresponding phase, ranging from $-\pi$ to $+\pi$. The earliest motion is represented by $+\pi$, and the latest motion is represented by $-\pi$. Data acquisition may be gated off the R wave of the ECG complex. An ECG may be used to provide any preliminary information that may be necessary regarding the cardiac cycle and major cardiac events within the cycle, e.g. the onset of systole and diastole.

In one embodiment, the phase image 32 is a frame of data that can be retained for further analysis in order to make determinations regarding operation of the heart. For example, comparisons can be made between the phase angles of different regions of interest.

In another embodiment, the phase imaging 32 may be a display of a single image or may be a dynamic cine loop. A single-image display may be formed by encoding each pixel in the image such that phase values from $+\pi$ to $-\pi$ are displayed from black to white. Since $+\pi$ represents the earliest motion and $-\pi$ represents the latest motion within the time series 16 of echocardiographic data frames, the single-image display 32 of timing will be one in which areas of later activity will be brighter than those of earlier activity. If a cardiac contraction is a motion down the septum from the base to the apex of the heart, around the apex and then up the free ventricular wall, the image will be a gray-scale image in which the free ventricular wall at the base will be shown as being brighter than the apex, which in turn will be brighter than the base of the septum.

Alternatively, the phase image 32 may be a dynamic cine loop of image frames. Individual pixels in a particular frame may be set to a particular color, e.g. red, if the onset of motion of the cardiac site represented by the pixel has occurred during or before motion at other cardiac sites. Where pixel values are assigned according to phase values from $+\pi$ to $-\pi$, the pixels may be set to display red if the pixel values fall within a specific window of pixel values. For example, the window may have a width of $2\pi$ divided by the number of frames in the cine loop, with movement from $+\pi$ to $-\pi$ in order to show forward progression of time. Thus, the number of frames in the cine loop determines the degree of detail obtained in viewing a contraction sequence. Once set red, the pixels may either "turn off" so that the cine loop displays a wavefront of motion, or the pixels may remain red for the duration of the cine loop in order to display motion that has occurred. Optionally, the cine loop may be overlaid with the gray-scale phase image described above in order to enhance anatomic visualization of the cardiac sequence.

For display purposes, static clutter and other cavity noise may be removed from the phase image 32 by filtering on the magnitude of the signal, filtering on the magnitude of the DC component, and filtering on the magnitude of the first harmonic. In the phase imaging, if the magnitude is less than a predetermined threshold, the phase angle is then suppressed. Generally, the first harmonic filter is better, since noise in the cavity is generally random and typically has no significant first harmonic component, even though it may have a significant magnitude.

We claim:

1. A method of monitoring performance of a heart comprising the steps of:

coupling echocardiographic equipment to a person such that myocardial motion in any direction can be detected;

selecting an interrogation region for detecting direction-independent myocardial motion of at least a portion of the heart;

obtaining echocardiographic signals from said interrogation region responsive to said direction-independent myocardial motion including collecting waves transmitted from said echocardiographic equipment and reflected from said at least a portion of the heart;

repeating said step of obtaining echocardiographic signals for each of a plurality of time intervals;

assessing speed of regions of interest of said heart in real-time based upon said echocardiographic signals, said step of assessing speed including determining the difference between echocardiographic signals obtained during a first time interval and corresponding echocardiographic signals obtained during a time interval adjacent to said first time interval, repeating said step of determining for each time interval in said plurality of time intervals, thereby obtaining a set of signal differences for each pair of adjacent time intervals, and determining a set of mean squared difference values for each said set of signal differences; and analyzing the operation of said heart based upon said speed of said regions of interest.

2. The method of claim 1 wherein obtaining said sets of signal differences includes forming a plurality of data frames from said echocardiographic signals, said frames having corresponding data points, and determining differences between corresponding data points of said frames in a data point-by-data point fashion.

3. The method of claim 2 wherein said step of determining said set of mean squared difference values includes squaring said signal differences and performing a step of ensemble averaging upon a resulting plurality of sets of squared signal differences.

4. The method of claim 1 wherein said step of analyzing said operation of said heart includes averaging speed over a desired period of time, thereby performing temporal averaging, said step of analyzing further including imaging cardiac operation by assigning pixel values in accordance with said temporal averaging to image cardiac operation as a function of regional average speed.

5. The method of claim 1 wherein said step of analyzing said operation of said heart includes determining peak speed during a desired period of time, thereby obtaining peak speeds, said step of analyzing further including imaging cardiac operation by assigning pixel values in accordance with said peak speeds, thereby imaging cardiac operation as a function of regional peak speeds.

6. The method of claim 1 wherein said step of analyzing said operation of said heart includes harmonic processing.

7. The method of claim 1 wherein said step of analyzing said operation includes determining the onset of motion at selected regions of said heart during a selected cardiac event and further includes assigning pixel values in accordance with said onset of motion to image said operation as a function of relative onset of motion.

8. The method of claim 1 wherein said step of analyzing said operation includes generating waveforms indicative of said speed of said regions of interest.

9. A method of monitoring performance of a heart comprising the steps of:

(a) transmitting ultrasonic wave energy into a patient in the direction of the patient's heart;

(b) receiving echo signals reflected from said heart;

(c) in response to said echo signals, forming a plurality of first data frames such that said first frames correspond to a sequence of images within a preselected period of time, said frames having sets of corresponding data points;

(d) for a first set of corresponding data points of said first frames, determining mean squared difference data, thereby assessing cardiac motion;

(e) repeating step (d) for various sets of corresponding data points of said first frames; and (f) analyzing said cardiac motion to monitor performance of said heart.

10. The method of claim 9 wherein said steps (d) and (e) include forming a plurality of second data frames $$\left(\frac{dS}{dt}\right)$$

by determining on a data point-by-data point basis the difference between data point values of sequentially adjacent first frames.

11. The method of claim 10 wherein steps (d) and (e) further include squaring said differences between said data point values, thereby obtaining a square rate of signal change $$\left(\frac{dS}{dt}\right)^2$$

for each data point of each second frame.

12. The method of claim 11 wherein said steps (d) and (e) further include forming a plurality of third frames on a frame-by-frame and data point-by-data point basis, said forming said third frames including averaging $$\left(\frac{dS}{dt}\right)^2$$

of each data point of said second frames with $$\left(\frac{dS}{dt}\right)^2$$

data point values of data points in a selected region of the second frame in which said each data point resides.

13. The method of claim 12 wherein step (f) includes determining a gradient $$\left(\frac{dS}{dg}\right)^2$$

between adjacent data points of each frame of said first frames.

14. The method of claim 13 wherein steps (d) through (f) further include forming a plurality of fourth frames from said third frames, said forming said fourth frames including using said gradient as a divisor to determine one of a root mean squared speed (m) and a mean squared speed ($v^2$).

15. The method of claim 14 further comprising forming an image of operation of said heart in response to averaging of corresponding data points of one of said third and said fourth frames.

16. The method of claim 14 further comprising forming an image of operation of said heart in response to peak data point values at corresponding data points of said fourth frames.

17. The method of claim 14 further comprising utilizing harmonic processing to monitor performance of said heart.

18. A system of monitoring performance of a heart comprising:

echocardiographic means for transmitting ultrasonic waves into a living body and for receiving echo signals sensitive to cardiac motion in all directions;

means in electrical communication with said echocardiographic means for recording a time series of first frames of direction-independent echocardiographic data in response to said echo signals;

means, operatively associated with said means for recording, for storing a series of second frames, said second frames having mean squared difference values derived from said direction-independent echocardiographic data recorded in said first frames;

means, operatively associated with said means for recording, for storing a series of third frames having mean squared gradient values derived from said echocardiographic data recorded in said first frames;

means, in data communication with said means for storing said second frames and said means for storing said third frames, for storing data derived from said second and third frames that is indicative of the speed of regions of said heart.

* * * * *